United States Patent
Zeng et al.

(10) Patent No.: US 11,097,066 B2
(45) Date of Patent: Aug. 24, 2021

(54) APPARATUS FOR MOUNTING A PEN NEEDLE ASSEMBLY

(71) Applicant: Becton, Dickinson and Company, Franklin Lakes, NJ (US)

(72) Inventors: Xi Zeng, Jiangs (CN); Huasheng Huang, Jiangsu (CN); Wei Hu, Shanghai (CN); Fei Wang, Shanghai (CN); Tingting Fan, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 265 days.

(21) Appl. No.: 16/465,784

(22) PCT Filed: Dec. 5, 2017

(86) PCT No.: PCT/US2017/064698
§ 371 (c)(1),
(2) Date: May 31, 2019

(87) PCT Pub. No.: WO2018/106680
PCT Pub. Date: Jun. 14, 2018

(65) Prior Publication Data
US 2020/0023140 A1    Jan. 23, 2020

(30) Foreign Application Priority Data

Dec. 6, 2016  (CN) .......................... 201611111494.6
Dec. 6, 2016  (CN) .......................... 201621333824.1

(51) Int. Cl.
*A61M 5/32* (2006.01)
*A61B 50/30* (2016.01)
(Continued)

(52) U.S. Cl.
CPC ....... *A61M 5/3204* (2013.01); *A61B 50/3001* (2016.02); *A61M 5/002* (2013.01);
(Continued)

(58) Field of Classification Search
CPC .. A61M 5/3204; A61M 5/002; A61M 5/3202; A61M 5/343; A61M 2005/3215;
(Continued)

(56) References Cited

U.S. PATENT DOCUMENTS 5,000,742 A   3/1991   Morrison
5,007,535 A   4/1991   Meseke et al.
(Continued)

FOREIGN PATENT DOCUMENTS

AU   2009202158 A1   12/2009
CN   102711872 A     10/2012
(Continued)

OTHER PUBLICATIONS

International Search Report dated Apr. 30, 2018, which issued in the corresponding PCT Patent Application No. PCT/US2017/064698.
(Continued)

*Primary Examiner* — Jacob K Ackun
(74) *Attorney, Agent, or Firm* — Dickinson Wright PLLC (57) ABSTRACT

A storage device (30) for storing a pen needle assembly (10) includes a housing (30) having first wells (44) with a dimension for receiving the pen needle assembly and second wells (46) for receiving an inner shield (24) of the pen needle assembly. The second wells (46) have a diameter less than a diameter of the first wells (44). An ejector (40) in the housing (34) can be actuated to eject the used needle hub (16) and outer covers (22) from the first well (44) and the inner shield (24) from the second well (46) for disposal. A method of coupling a pen needle delivery device to a needle hub is also provided.

17 Claims, 11 Drawing Sheets

(51) Int. Cl.
*A61M 5/34* (2006.01)
*A61M 5/00* (2006.01)
*A61B 50/36* (2016.01)

(52) U.S. Cl.
CPC .......... *A61M 5/3202* (2013.01); *A61M 5/343* (2013.01); *A61B 50/362* (2016.02); *A61M 2005/3215* (2013.01); *A61M 2005/3254* (2013.01); *A61M 2205/586* (2013.01)

(58) Field of Classification Search
CPC .... A61M 2005/3254; A61M 2205/586; A61B 50/3001; A61B 50/362
USPC .................................................. 206/366, 365
See application file for complete search history.

(56) References Cited

U.S. PATENT DOCUMENTS

| | | | | |
|---|---|---|---|---|
| 6,923,318 | B1* | 8/2005 | Erickson | A61B 42/00 206/366 |
| 2002/0020647 | A1* | 2/2002 | Groth | B65D 83/02 206/366 |
| 2005/0269226 | A1 | 12/2005 | Erickson et al. | |
| 2005/0277896 | A1 | 12/2005 | Messerli et al. | |
| 2007/0119740 | A1* | 5/2007 | Clegg | A61M 5/008 206/366 |
| 2009/0014462 | A1 | 1/2009 | Costa et al. | |
| 2012/0145577 | A1* | 6/2012 | Bode | A61M 5/3276 206/366 |
| 2012/0302965 | A1 | 11/2012 | Cronenberg | |
| 2013/0341224 | A1* | 12/2013 | Dasbach | A61M 5/3205 206/366 |
| 2014/0138268 | A1* | 5/2014 | Dasbach | B65D 85/24 206/366 |
| 2014/0367288 | A1* | 12/2014 | Ziegner | A61M 5/002 206/366 |
| 2016/0022540 | A1* | 1/2016 | Rodriguez | A61J 7/0069 206/366 |

FOREIGN PATENT DOCUMENTS

| | | |
|---|---|---|
| CN | 102791309 A | 11/2012 |
| CN | 207119035 U | 3/2018 |
| JP | 2015139623 A | 8/2015 |

OTHER PUBLICATIONS

Ohinese Office Action dated Dec. 25, 2020, which issued in the corresponding Chinese Patent Application No. 201611111494.6, including English translation.

Extended European Search Report dated Jun. 9, 2020, which issued in the corresponding European Patent Application No. 17877669.6.

* cited by examiner

APPARATUS FOR MOUNTING A PEN NEEDLE ASSEMBLY

This application claims priority under 35 U.S.C. § 119(a) from Chinese Utility Model Application No. 201621333824.1, filed on Dec. 6, 2016, and Chinese Invention Patent Application No. 201611111494.6, filed on Dec. 6, 2016, which are hereby incorporated herein by reference in their entirety.

FIELD OF THE INVENTION

The present invention relates generally to an apparatus for use in mounting a pen needle assembly to a pen delivery device. More particularly, the present invention generally relates to an apparatus having a first well to retain a needle hub with an inner shield and to retain the needle hub after use to reduce the risk of inadvertent needle stick. The apparatus can have a second well to receive the inner shield for separating the inner shield from the needle hub without the need to handle the inner shield.

BACKGROUND OF THE INVENTION

Insulin and other injectable medications are commonly delivered with drug delivery pens, whereby a disposable pen needle hub is attached to the pen to facilitate drug container access and allow fluid egress from the container through the needle into the patient.

Various pen needle delivery devices are known in the art for dispensing the substance to the patient. The delivery devices often use a disposable needle hub having a cannula or needle extending from a patient end of the hub for inserting into the patient. A non-patient end of the hub is coupled to the pen delivery device for delivering the substance to the patient.

The needle hub assembly is often packaged in a container containing several loose needle hubs. A needle hub is selected from the package and attached to the pen needle delivery device for injecting the patient and then removed to be discarded. The needle hub package includes an outer cover that encloses the needle hub and a removable seal that is peeled from the outer cover to open the cavity so that the needle hub can be removed. The needle hub can have a threaded non-patient end that is threaded onto the delivery device. The delivery device with the attached needle hub is then removed from the outer cover. An inner needle shield is attached to the needle hub to cover the cannula until the device is ready for use. The shield is removed to expose the cannula for use to deliver the substance to the patient. After use, the needle hub can be inserted back into the outer cover to enclose the exposed cannula. The pen delivery device is separated from the needle hub leaving the needle hub within the outer cover.

The prior devices require the use of both hands to connect to and remove the needle hub from the delivery device. During the placement back into the outer cover, the cannula is exposed and provides an increased risk of accidental needle stick. The manual operation of holding the outer cover while positioning the spent needle hub and cannula into the cavity of the outer cover can be difficult without accidental needle stick.

Existing pen needle assemblies are disclosed in U.S. Patent Application Publication Nos. 2006/0229562 to Marsh et al. and 2007/0149924 to R. Marsh, the entire contents of both of which are hereby incorporated by reference.

Although the prior devices have been suitable for the intended use, there is a continuing need in the industry for improved packaging for a pen needle hub assembly.

SUMMARY OF THE INVENTION

An apparatus and device are disclosed for receiving at least one pen needle hub assembly. In particular, the one feature is directed to a package or apparatus for a pen needle assembly that can be used in a manner to reduce the risk of inadvertent needle stick.

In one embodiment, the apparatus is provided with a well for a needle hub to retain and support the needle hub and cannula while attaching to a pen needle delivery device and storing a used needle hub for disposal. The apparatus has a recess or well for receiving an inner shield that covers the cannula so that the inner shield can be removed from the needle hub without the operator handling the inner shield. The used needle hub can be inserted back into the well and stored until ready for disposal. An ejector mechanism is provided to eject the needle hub, outer cover and inner shield to a suitable disposal such as a sharps container.

In accordance with another aspect of the apparatus, the inner shield can be inserted into a well in the apparatus so that the inner shield is retained by a friction fit or interference fit. The needle hub and cannula can then be pulled away to separate the inner shield while the inner shield is retained in the well without the need for the user to handle the inner shield.

One aspect of the apparatus is to provide a device for receiving and supporting a needle hub assembly to attach the needle hub to the delivery device without the need for the user to handle the exposed hub with the exposed cannula on the needle hub. The needle hub assembly is positioned in the device so that the delivery device can be attached to the non-patient end of the needle hub. An inner needle shield on the needle hub can then be inserted into a well in the device to grip the inner shield so that the inner shield can be separated from the needle hub without handling the inner shield. After use, the needle hub is positioned in a well of the device and disconnected from the delivery device where the device retains the used needle hub, outer cover, and inner shield. The needle hub can be retained in the needle hub well by a friction fit or interference fit to enclose the cannula and reduce the risk of inadvertent needle stick. An ejector is provided to eject the used components from the device into a disposal container.

The various features of the apparatus are basically attained by providing a device for a pen needle assembly where the pen needle assembly includes an outer cover, a needle hub, and an inner shield covering a cannula on the needle hub. The device comprises a housing having a top wall and a side wall. The top wall has an outer top surface with a least one first well with a dimension for receiving the pen needle assembly. A second well is formed in the top wall and has a diameter less that a diameter of the first well and a dimension for receiving and retaining the inner shield. The device includes an ejector for ejecting the outer cover and needle hub from the first well and for ejecting the inner shield from the second well.

In one embodiment, the second well has a dimension to receive the inner shield by a friction fit or interference fit so that inserting the inner shield into the well grips the inner shield with a sufficient force so that the needle hub when attached to the pen needle delivery device can be pulled outward to separate the inner shield to expose the cannula for delivering a substance to a patient. After use of the needle hub and cannula, the needle hub is inserted into the first well where the needle hub can be gripped by a friction fit or interference fit so that the pen needle delivery device can be separated from the needle hub without the operator handling the needle hub thereby reducing the risk of inadvertent needle stick.

The features of the apparatus are further attained by providing a device comprising a housing having a top wall with an outer top face. The top wall includes a plurality of first wells having a first dimension and a plurality of second wells with a second dimension. Each first well receives a pen needle assembly having an outer cover, a needle hub having a cannula, and inner shield coupled to the needle hub to enclose the cannula. The second well has a dimension for receiving and retaining the inner shield. The device further includes an ejector for ejecting the outer cover and used needle hub received in the first well and for ejecting the inner shield received in the second well.

The features of the invention are further attained by a method of coupling the needle hub of a pen needle assembly to a delivery device using a support device. The device has a top wall with a plurality of first wells for containing the pen needle assembly, a plurality of second wells with a dimension for receiving an inner shield of the pen needle assembly, and an ejector for ejecting the outer cover of the pen needle assembly and needle hub from the first wells and ejecting the inner shields from the second wells. The method includes the steps of inserting the coupling end of the delivery device into a first well to engage and couple to the open end of the needle hub. The delivery device with the needle hub attached is removed leaving the outer cover retained in the first well. The inner shield is inserted into the second well where the inner shield is gripped with sufficient force that the needle hub can be pulled free and separated from the inner shield to expose the cannula for use in delivering the substance to the patient. After use, the needle hub is inserted into the outer cover that was retained in the first well and disconnected from the delivery device. The ejector is then actuated to eject the used needle hub and outer cover from the first wells and eject the inner shields from the second wells for disposal.

The objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components, and structures.

DETAILED DESCRIPTION OF THE EXEMPLARY EMBODIMENTS

The present apparatus is directed to a device for storing and supporting at least one and preferably a plurality of pen needle assemblies for use with a pen delivery device. The apparatus is further directed to a storage device for a used needle hub where the used needle hub can be replaced in the device after use and later discarded without handling the needle hub to reduce the risk of accidental needle stick.

It will be understood by one skilled in the art that this disclosure is not limited in its application to the details of construction and the arrangement of components set forth in the following description or illustrated in the drawings. The embodiments herein are capable o of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The device for the needle hub assemblies can enable the convenient and easy assembly and removal of the needle hub on the pen delivery device with reduced handling of the exposed needle cannula. The device for the needle hub assemblies can be placed on a flat surface, such as a table, so that the pen needle delivery device can be attached to the needle hub assembly with one hand thereby reducing the risk of the needle stick by handling the needle hub with the exposed needle cannula.

Figure 1:
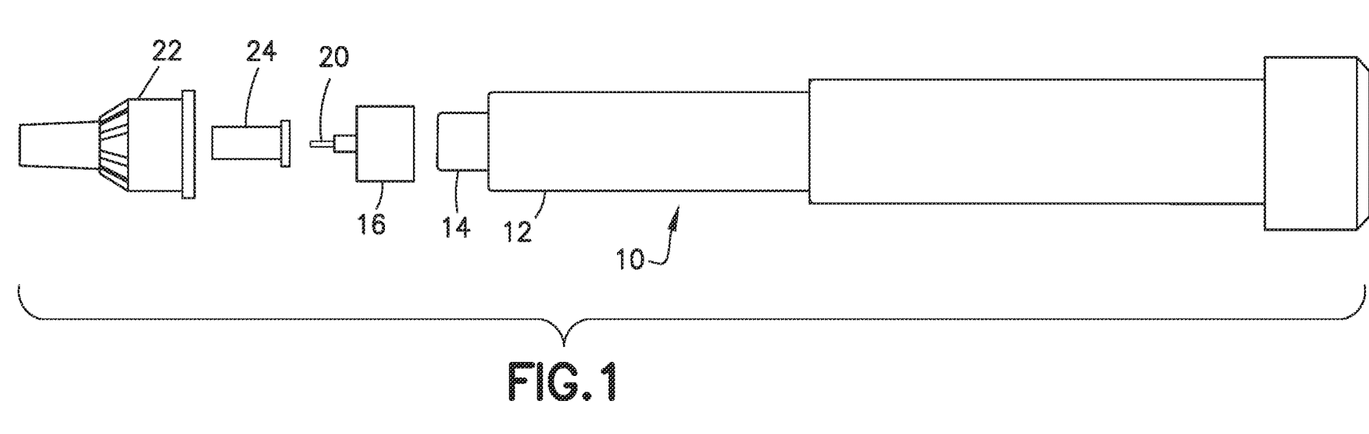
FIG. 1 is an exploded view of a pen needle delivery device in one embodiment showing the pen needle assembly that includes a needle hub, inner shield and cover.

Pen needle delivery device 10, as shown in FIG. 1 typically comprises a dose knob/button, an outer sleeve 12, and a cap. A dose knob/button allows a user to set the dosage of medication to be injected. The outer sleeve 12 is gripped by the user when injecting medication. The cap is used by the user to securely hold the pen injector device 10 in a shirt pocket, purse or other suitable location and provide cover/protection from accidental needle injury.

Figure 2:
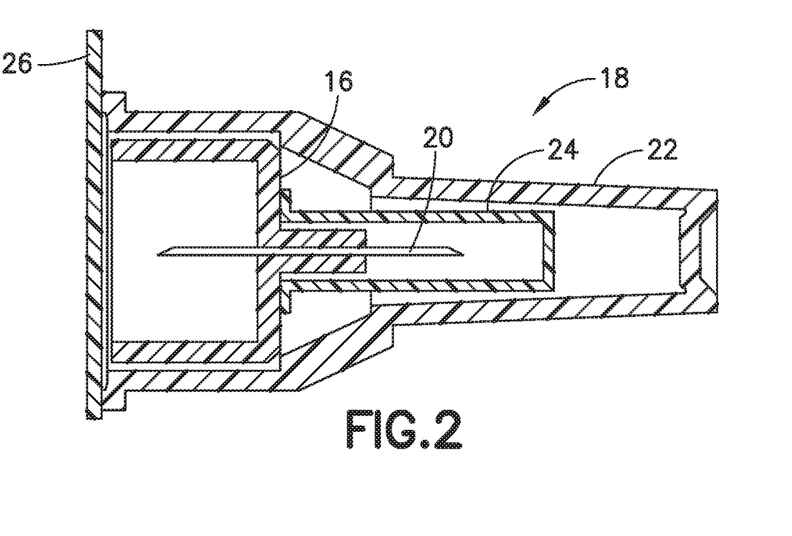
FIG. 2 is a cross-sectional view of the pen needle assembly.

In standard pen needle delivery devices the dosing and delivery mechanisms are all found within the outer sleeve 12 and is not described in greater detail here as they are understood by those knowledgeable of the prior art. A medicament cartridge is typically attached to a standard pen injector housing by known attachment means. The distal movement of a plunger or stopper within the medicament cartridge causes medication to be forced into the reservoir housing. The medicament cartridge is sealed by a septum and punctured by a septum penetrating needle cannula located within a reservoir or housing. Reservoir housing is preferably screwed onto the medicament cartridge although other attachment means can be used. The pen needle delivery device can be a standard pen delivery device known in the industry so that the pen needle delivery device is not shown in detail. The pen needle assembly 18 as shown in FIG. 2 includes a needle hub 16 supporting a cannula 20, an outer cover 22, and an inner shield 24. A protective seal 26 is attached to the open end of the outer cover as shown in FIG. 2 to enclose the needle hub and cannula to maintain a clean and sterile condition. The seal can be a label or other closure member that can be easily peeled from the outer cover to access the needle hub during use.

The pen needle delivery device 10 is connected to needle hub 16 shown in FIG. 1 that has a connecting non-patient end with internal threads that screw onto a threaded end 18 of the delivery device 10. A needle cannula 20 extends from the patient end of the needle hub 16 for delivering the substance to the patient. The outer cover 22 can be provided to cover the needle cannula to protect the patient from accidental needle stick before and after use. The inner shield 24 is provided over a post extending from the end of the needle hub 16 to enclose the cannula. During use, the needle hub 16 is connected to the pen delivery device and the inner shield is removed. After use, the outer cover is generally placed back on needle hub to cover the needle cannula. The needle hub with the cover is then removed from the pen needle delivery device and discarded.

The device is configured for receiving and supporting at least one pen needle assembly in a position where the delivery device or pen needle injector device can be coupled to the needle hub for use for injecting the substance to the patient without the need for the user to handle the needle hub with the exposed cannula. The used needle hub and cannula can then be positioned back into the outer cover that is retained in the device and separated from the delivery device. The used outer cover and needle hub and the inner shield are retained in the device. The device can then be inverted and an ejector actuated or deployed to eject the used outer cover, needle hub and inner shield for safe disposal without handing the components.

Figure 3:
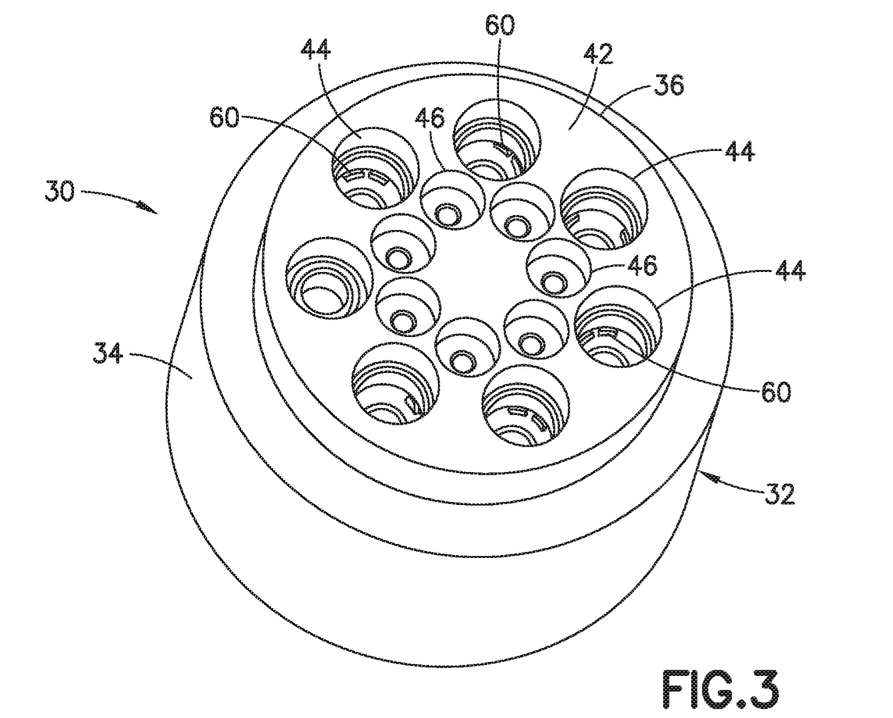
FIG. 3 is a top perspective view of the storage device in one embodiment.
Figure 4:
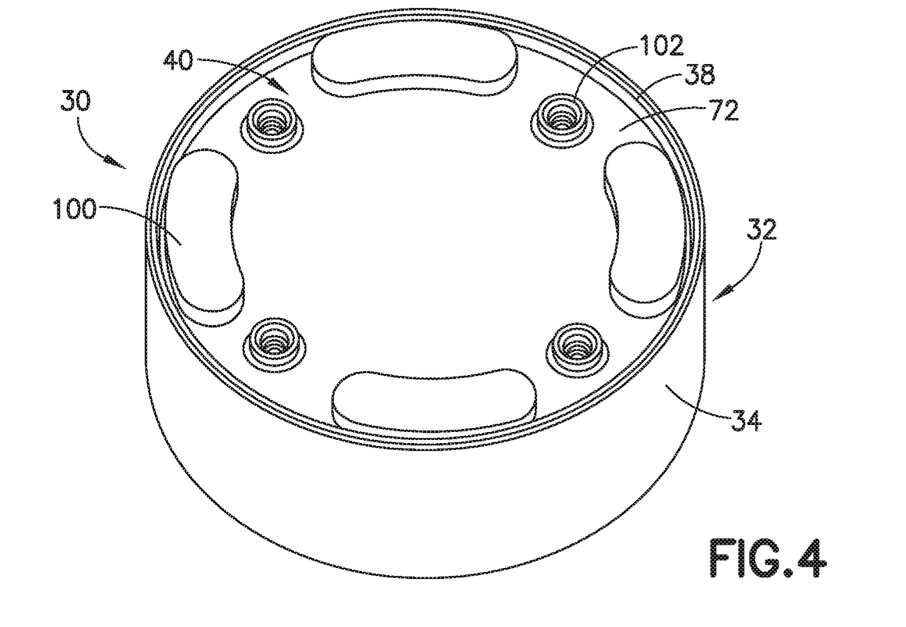
FIG. 4 is a bottom perspective view of the storage device of FIG. 3 showing the gripping members.
Figure 5:
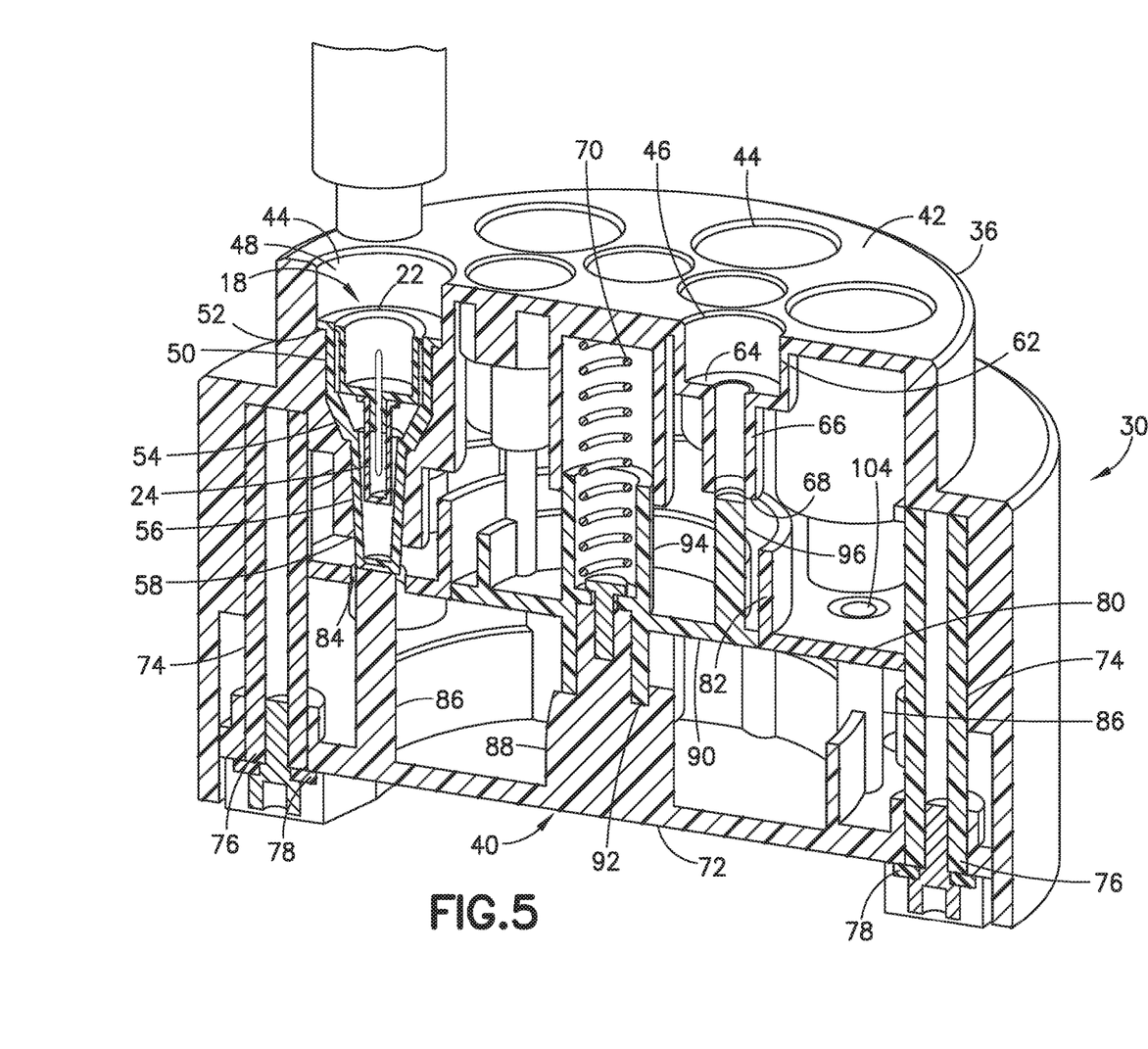
FIG. 5 is a cross-sectional view of the storage device showing the pen needle assembly positioned in the well.

Referring to FIGS. 3-5, the supporting device 30 of the invention including a housing 32 with a side wall 34, a top wall 36, an open bottom end 38 and an ejector 40 received in the open bottom end 38. Top wall 36 has an outer top face 42 with at least one and preferably a plurality of recesses that form wells for the pen needle assembly. In the embodiment shown, top wall 36 has a plurality of first wells 44 spaced apart from each other and facing outward from top face 42. Each well 44 has a dimension to receive and support a pen needle assembly and shown in FIG. 5. A plurality of second wells 46 are also provided in the top wall 36 and spaced from the first wells 44. The second wells 46 have dimension to receive and support an inner shield 24.

In the embodiment shown and described, the wells 44 and 46 are formed in the top wall 36. In other embodiments, the well can be provided in a side wall or other location that is accessible to the user. Providing the wells in the top wall has an advantage that the delivery device can be pushed in a downward direction to inhibit movement of the device when placed on a stable surface or support.

As shown in FIG. 5, the wells 44 for the pen needle assembly depth and width complementing the dimensions of the pen needle assembly 18. The well 44 has a first substantially cylindrical upper section 48 with a diameter sufficient to receive the pen needle assembly 18 and the threaded coupling end 14 of the delivery device 10. A second cylindrical section 50 is spaced below the first section 48 and spaced from the top wall 36. The section 50 has a diameter less that the diameter of the first section 48 with a ledge 52 extending between the first section 48 and second section 50 for mating with a shoulder on the delivery device. The ledge 52 is spaced from top wall 36 a distance to recess the outer flange 54 of the needle hub 16 below the top face 42. The ledge 52 forms a stop member for the outer cover 22 of the pen needle assembly and for the delivery device.

A conical section 54 extends from a bottom end of the second section 50 to converge to a lower section 56. As shown in the drawings, the lower section 56 has an open bottom end 58. Lower section 56 has a shape complementing the end of the outer cover 22. In the embodiment shown, lower section 56 has a slight taper or conical shape corresponding to the conical shape of the end of the outer cover. The first well 44 defined by the various sections has a shape and dimension complementing the shape and dimension of a pen needle assembly so that the pen needle assembly fits within the well 44.

In one embodiment shown in FIG. 3, a plurality of teeth 60 project inwardly from the bottom end of the second section 50 to mate with corresponding ribs or recesses formed in the outer surface of outer cover 22 shown in FIG. 1. The teeth 60 are oriented to engage the outer cover to inhibit rotational movement of outer cover 22 with respect to housing 32 while coupling and uncoupling the needle hub 16 from the coupling end of the delivery device. Well 44 can have a dimension to retain outer cover 22 by a friction fit or by an interference fit. In other embodiments, a gripping member can be provided to grip outer cover 22. In one embodiment the gripping mechanism can be an O-ring received in an annular recess in well 44 to engage the outer surface of outer cover 22.

In the embodiment shown, a plurality of the first wells 44 is formed in the top wall 36 for accommodating a plurality of pen needle assemblies. The first wells 44 can be arranged in a suitable pattern as needed. In the embodiment shown, the first wells 44 are arranged in a generally circular pattern around the outer edge of the top wall 36.

The second wells 46 have a shape and dimension to receive the inner shield 24 after separating from the needle hub 16. As shown in FIG. 5, well 46 has a first substantially cylindrical section 62 extending from the top face 42 and has a diameter complementing the outer diameter of the coupling end 14 so that only the coupling end 14 can be inserted into the well 46. First section 62 has an axial length corresponding to the length of the coupling end 14. A ledge 64 extends radially inward from a bottom end of first section 62 to a lower substantially cylindrical section 66. Lower section 66 extends from ledge 64 in an axial direction to an open bottom end 68. Lower section 66 has a diameter corresponding to the outer diameter of inner shield 24. In one embodiment, the diameter of lower section 66 has a diameter to form a friction fit with inner shield 24 to grip inner shield 24 to enable inner shield 24 to be separated from the post of needle hub 16.

Ejector 40 is mounted within the open bottom end 38 of housing 32 for sliding in an axial direction with respect to housing 32. In the embodiment shown, ejector 40 is biased away from top wall 36 by a spring member 70 extending between top wall 36 and ejector 40. Ejector 40 is formed by a bottom plate 72 having an outer dimension to fit within the open bottom 38 and to slide within housing 32. Housing 32 includes guide posts 74 extending in the axial direction to the bottom end of housing 32. Bottom plate 72 is provided with openings 74 that receive the guide posts 76 for sliding movement relative to the housing 32. A stop member 78 is provided on each guide post 76 to retain bottom plate 72 within the cavity of housing 32 while allowing sliding movement of bottom plate 72.

Figure 6:
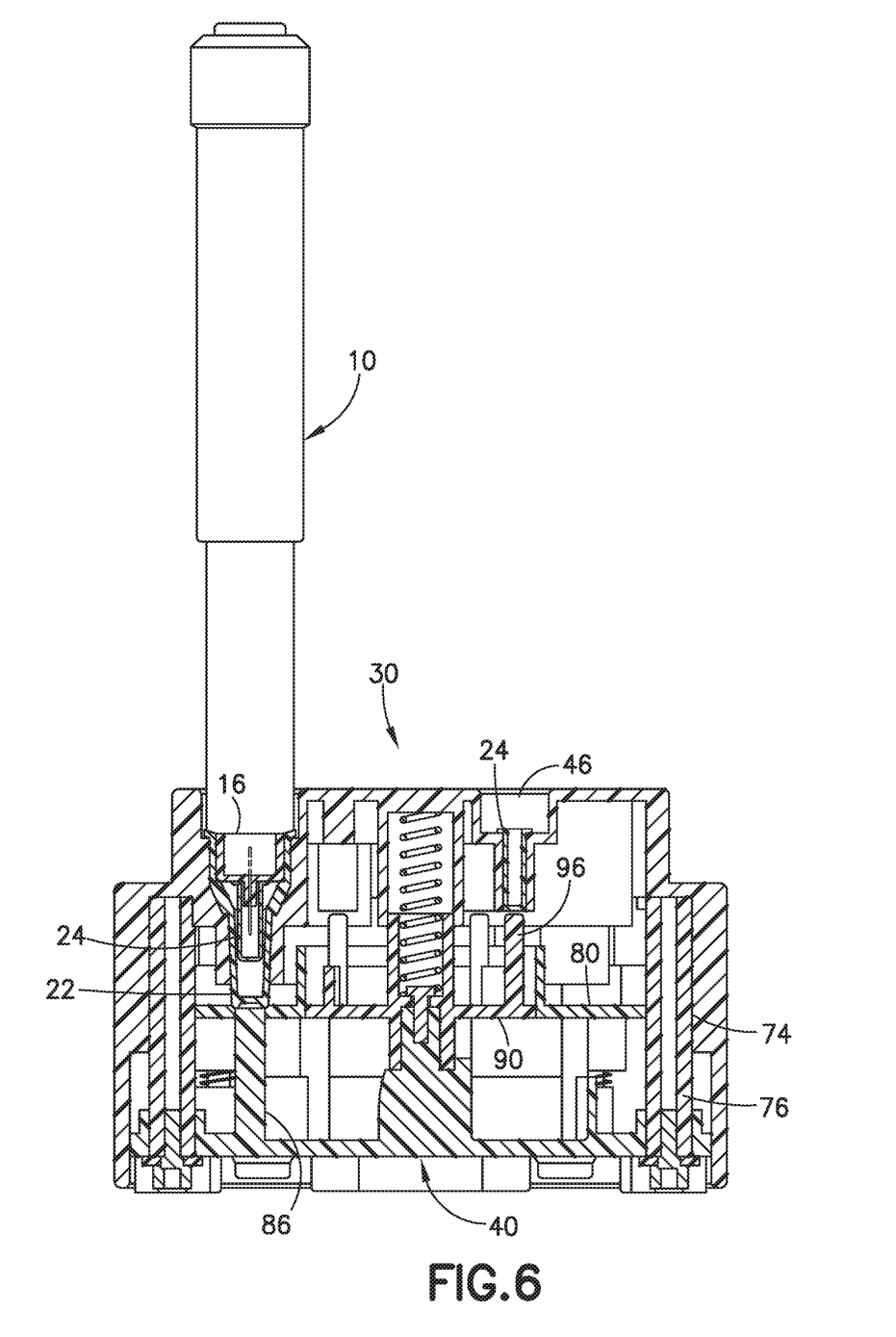
FIG. 6 is a cross-sectional view of the device showing the delivery device being connected to the needle hub.

Housing 32 has a flange 80 extending radially inward from side wall 34 toward the axial center of housing 32 and is positioned between the top and bottom ends of the side wall. An axially extending inner wall 82 extends in an upward direction toward top wall 36 and is spaced radially inward from and parallel to side wall 34. Flange 80 includes an aperture 84 aligned with and receives a plunger 86 extending from bottom plate 72. As shown in FIG. 6, plunger 86 is aligned with the open bottom end 58 of first well 44 for sliding movement within first well 44 with the sliding movement of ejector 40. Flange 80 includes an aperture 104 aligned with each well 44. A plunger 86 for each well 44 is provided on bottom plate 72.

Ejector 40 includes a center post 88 extending upwardly from bottom plate 72 toward top wall 36 for supporting a plate 90. Plate 90 has a substantially flat configuration with an outer dimension corresponding to an inner dimension of inner wall 82 for sliding axially within the cavity of inner wall 82. A lower sleeve 92 extends from a bottom face of plate 90 for coupling with center post 88 and an upper sleeve 94 for mating with the spring 70. A plunger 96 extends from the upper face of plate 90 and is aligned with the open bottom end 68 of second well 46 for sliding through well 50. Each well 46 is provided with a corresponding plunger 96. As shown in FIG. 5, spring 70 biases ejector 40 away from top wall 36 so that plunger 86 and plunger 96 are in a retracted position so that the components of the pen needle assembly can be inserted into the respective well. The ejector can be manually pushed upward so that the plunger 86 and plunger 96 are in a second position shown in FIG. 13 to eject the components from the respective wells.

The bottom face of the device 30 can include a slip-resistant surface or friction member to resist sliding when placed on a surface such as table top. The embodiment shown, the bottom face of bottom plate 72 is provided with slip resistant pads 100 and suction-like cups 102 for stabilizing the device on a supporting surface during use. In other embodiments, the bottom edge of side wall 34 of housing can be provided with a suitable non-slip surface or member.

The support device 30 of the invention is used for coupling and un-coupling a needle hub to a pen needle delivery device in a manner that reduces the risk of accidental needle stick by avoiding the need for the user to handle the needle hub with an exposed cannula. The device also provides a convenient method of storing used needle hubs and discarding the used needle hubs in a safe manner.

Figure 7:
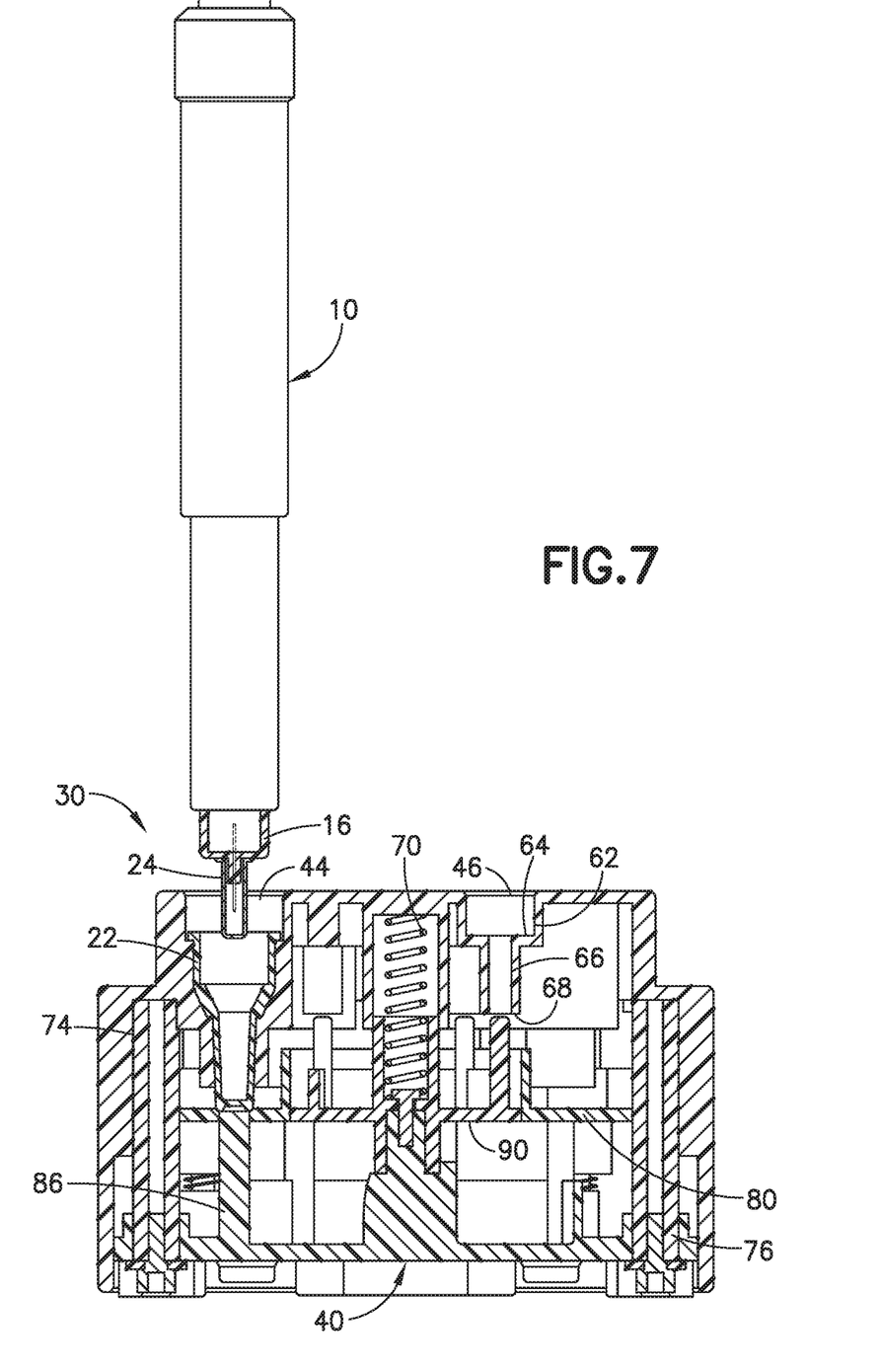
FIG. 7 is a perspective view of the device showing the needle hub being pulled from the outer cover.

The device is suitable for use in a method of coupling and uncoupling a delivery device to a needle hub and disposing of used needle hubs with reduced exposure by the user to the cannula after the injection. In use, the seal 26 can be removed from a pen needle assembly 18 and the pen needle assembly is positioned in a selected well 44 so that the assembly is positioned below the top face 42 of device 30 as shown in FIG. 5. In other embodiments, the pen needle assembly 18 with the seal attached can be placed in the well 44. In one embodiment, a seal or closure can be provided on the open top end of the well 44 to protect the needle hub received in the well. The seal can then be removed or separated from the outer cover prior to use. A delivery device 10, such as a conventional pen needle delivery device, is inserted into well 42 as shown in FIG. 6. Teeth 60 engage the outer surface of outer cover 22 so that coupling end 14 of delivery device 10 can be coupled to needle hub 16. In the embodiment shown, the coupling end 14 has external threads for mating with internal threads on the inner surface of needle hub 16 as known in the art. Delivery device 10 can be rotated within well 44 to screw the coupling end 18 into needle hub 16. Delivery device 10 with the needle hub 16 attached is then retracted from the well 44 with the inner shield 24 attached to the end of needle hub 16 while the outer cover 22 remains captured within the well 44 as shown in FIG. 7.

Figure 8:
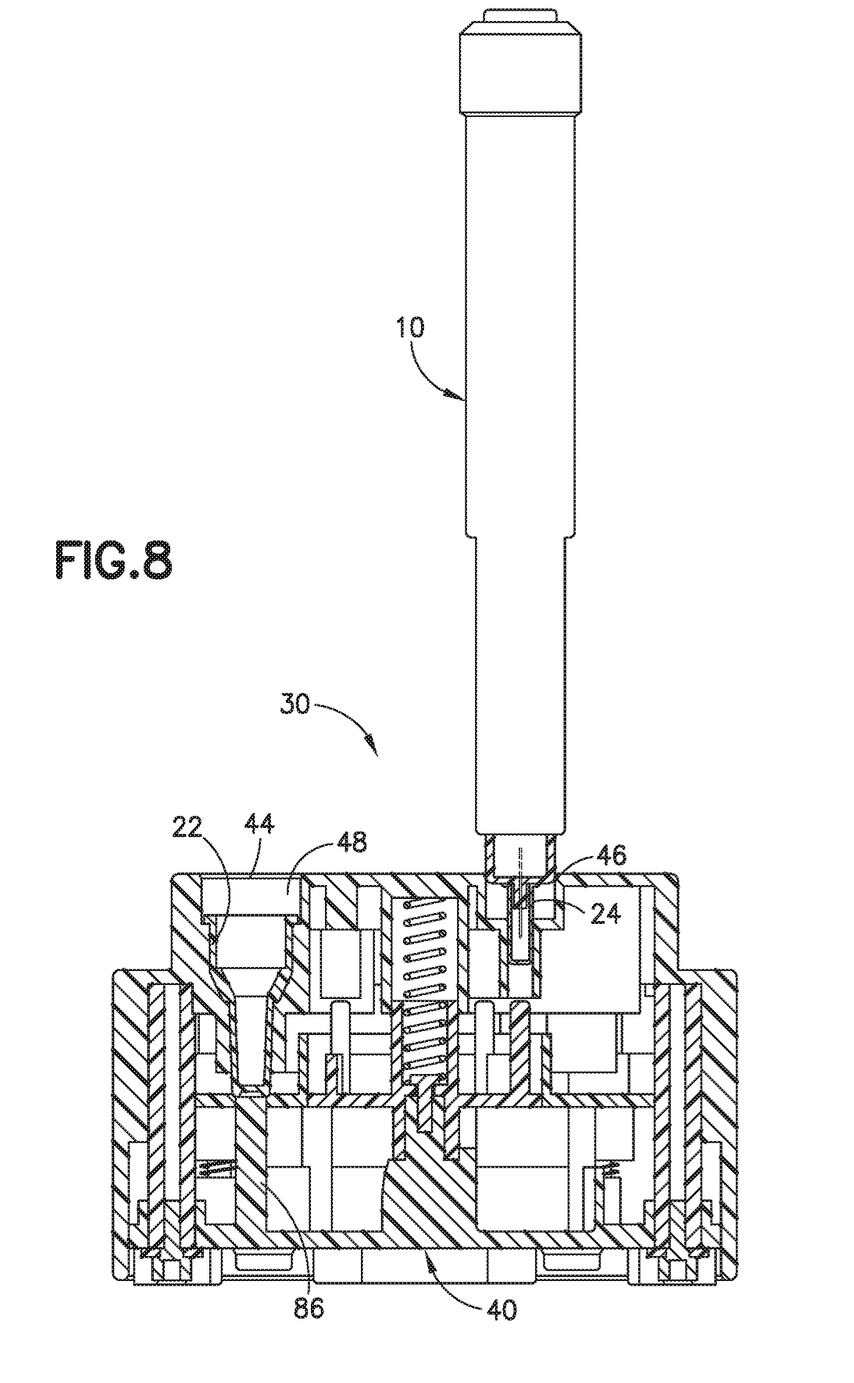
FIG. 8 is cross-sectional view of the pen needle delivery device inserting the inner shield into the well of the device.
Figure 9:
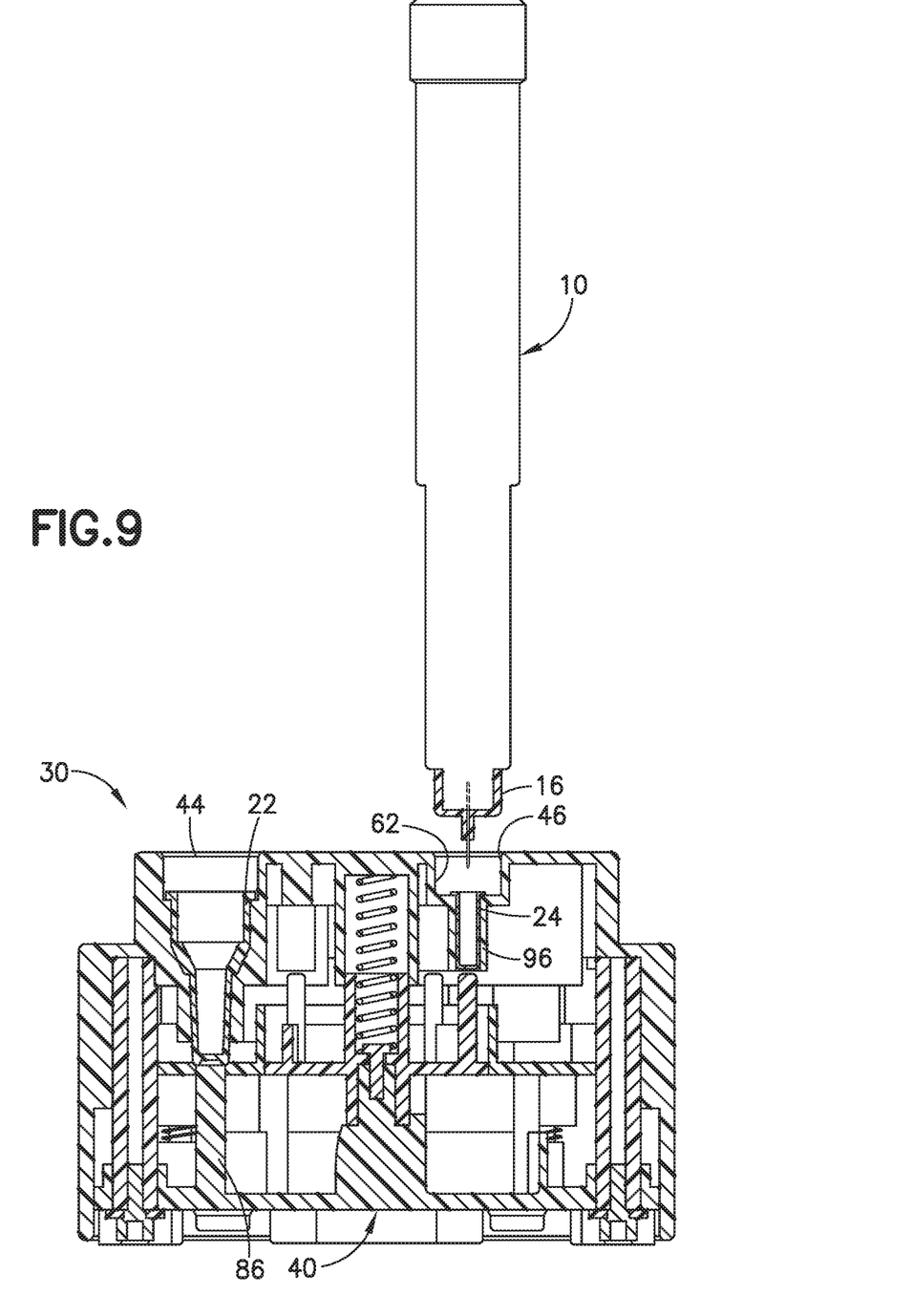
FIG. 9 is a cross-sectional view of the pen needle delivery device being separated from the inner shield.

Referring to FIG. 8, delivery device 10 with the needle hub 16 and inner shield 24 is inserted into well 46 so that inner shield 24 is positioned in second section 66 of well 46. Second section 66 of well 44 has a dimension or other gripping mechanism to grip inner shield 24 so that delivery device can be withdrawn leaving inner shield 24 within well 46 as shown in FIG. 9. In this manner, a needle hub can be coupled to a delivery device with limited handing of the needle hub and without the need to manually remove the outer cover and inner shield to expose the cannula. The delivery device with the exposed cannula shown in FIG. 9 is ready for use to inject the substance into the patient.

Figure 10:
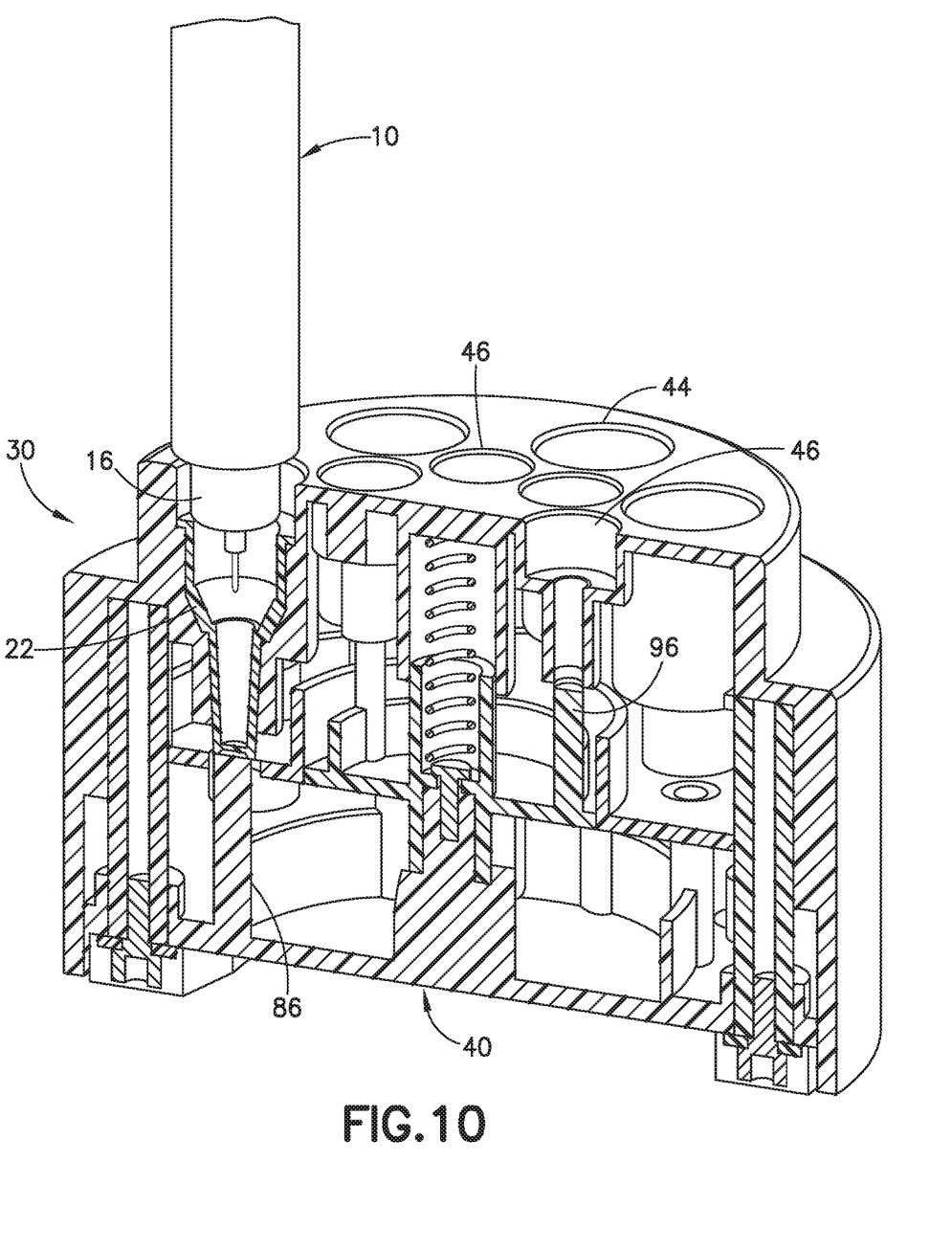
FIG. 10 is a cross-sectional view of the needle hub being inserted into the outer cover that is retained in the well.
Figure 11:
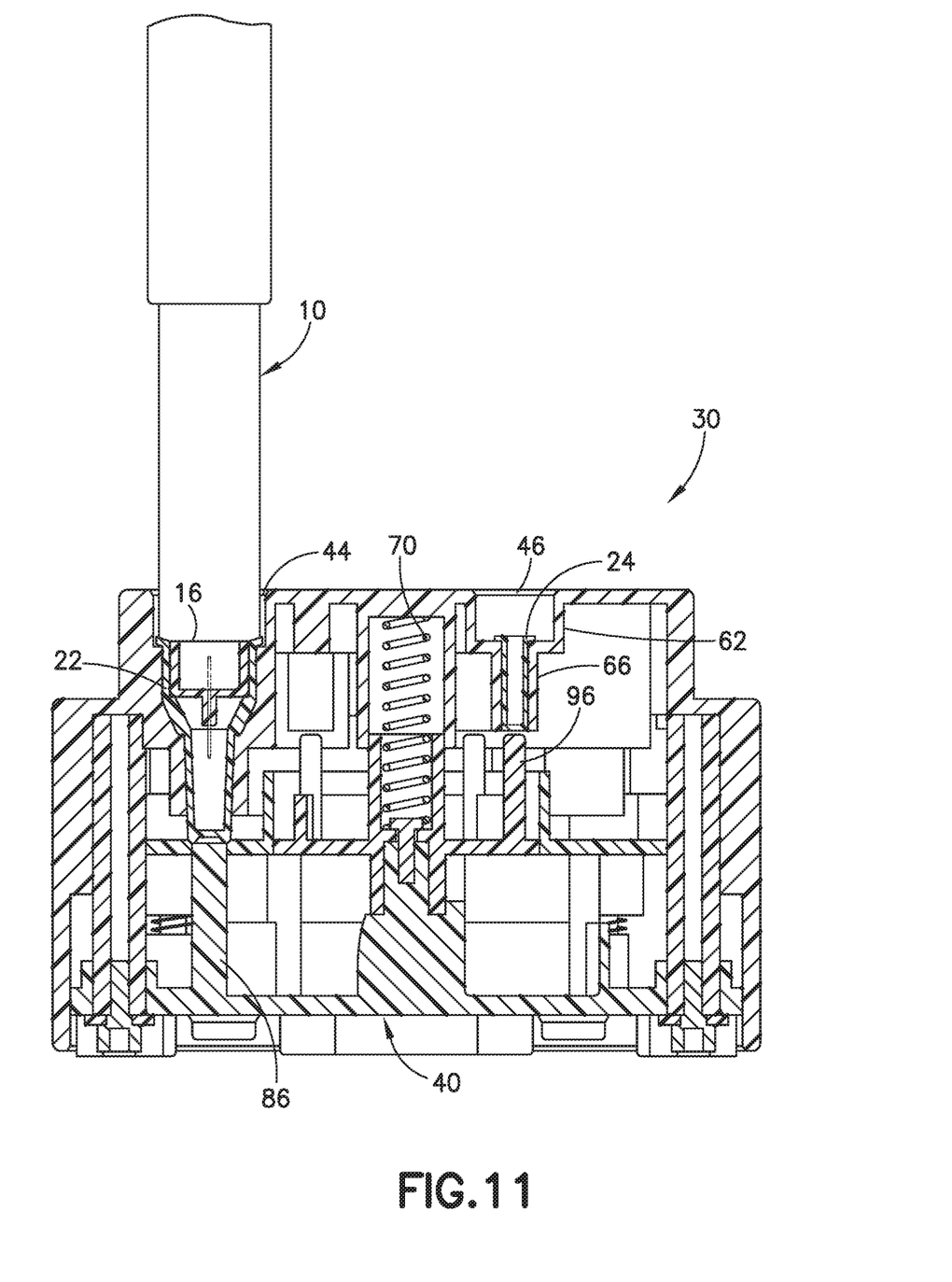
FIG. 11 is a cross-sectional view showing the needle hub positioned within the outer cover after use.
Figure 12:
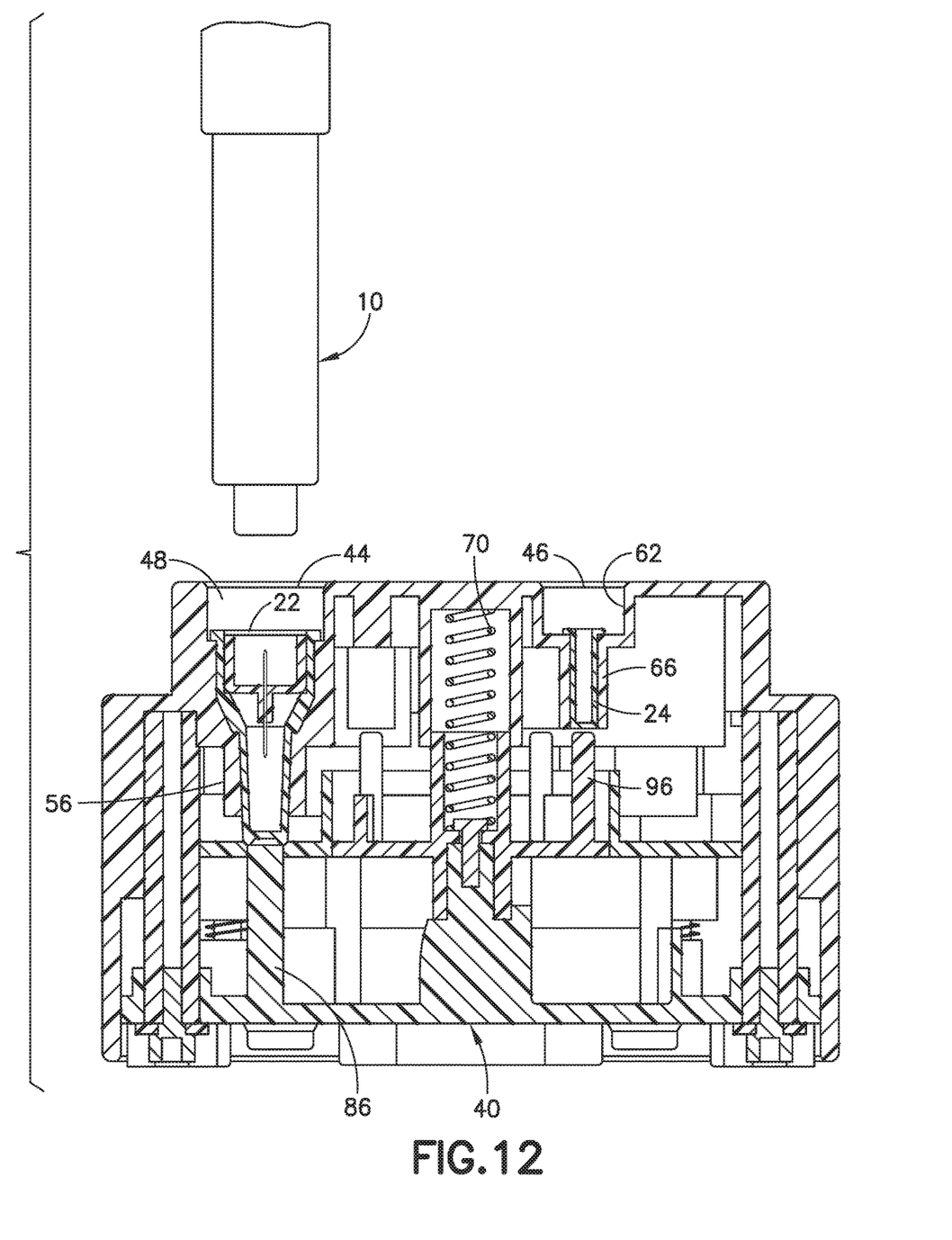
FIG. 12 is a cross-sectional view showing the delivery device separated from the used needle hub.

After use, the used needle hub 16 can be placed back into the outer cover 22 without the need for the user to handle the outer cover or the needle hub. Referring to FIGS. 10 and 11, the used needle hub 16 while attached to the delivery device 10 is inserted into the first well 44. As shown in FIG. 11, the needle hub 16 is inserted back into the outer cover 22 where the delivery device can be rotated to unscrew the coupling end 14 from needle hub 16. Delivery device 10 can then be removed as shown in FIG. 12 for further use.

Figure 13:
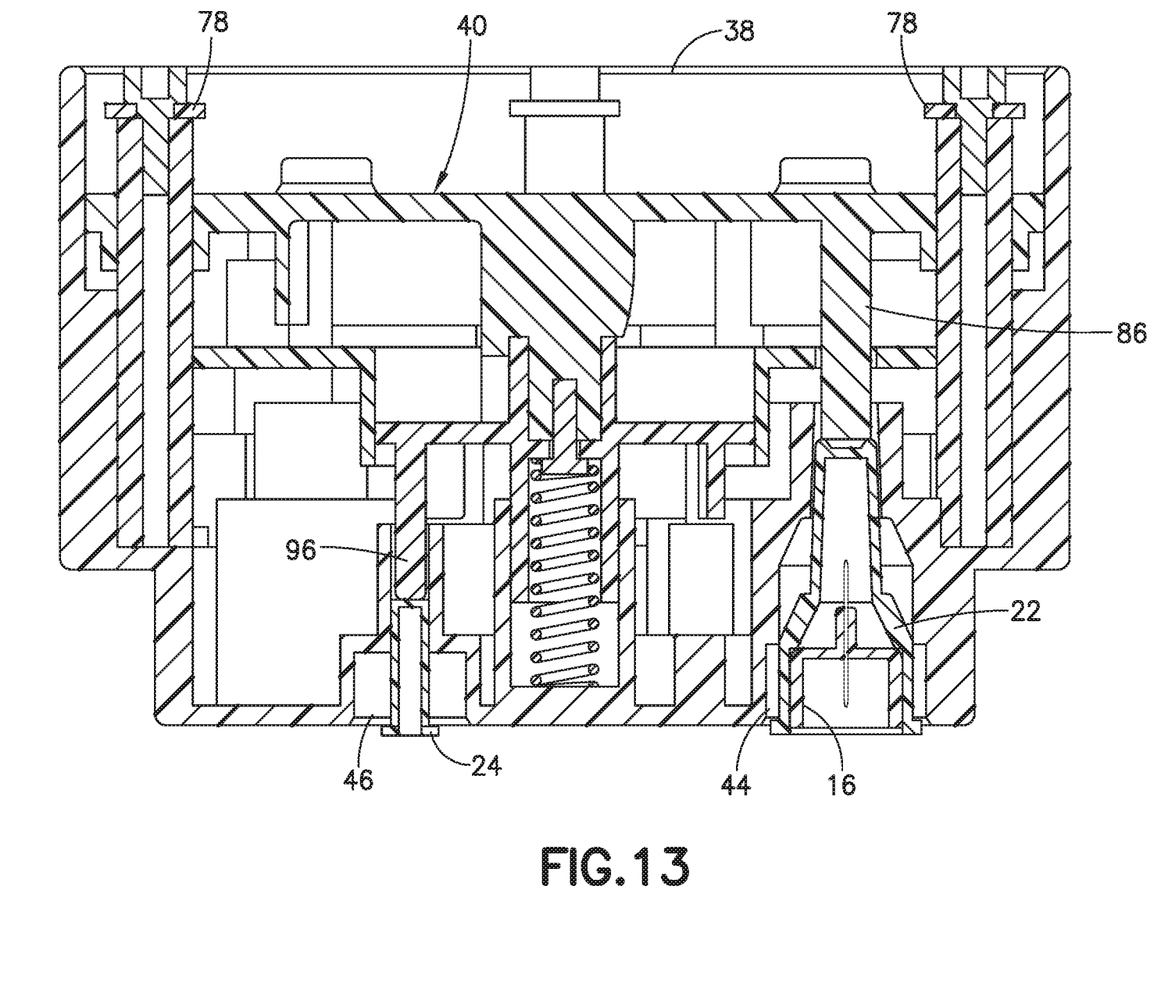
FIG. 13 is a cross-sectional view showing the ejector in a position for ejecting the used needle hub, outer cover and inner shield from the device.

The supporting device 30 of the invention is able to retain several used needle hubs 16 and the corresponding inner shields 24 in the respective wells to reduce the risk of accidental needle stick. The used needle hub 16 and inner shields 24 can be discarded by inverting the device 10 as shown in FIG. 13. The ejector 40 can be actuated and moved to the position shown in FIG. 13 where plungers 86 eject the outer covers 22 with the used needle hubs 16 and the plungers 96 eject the inner shields 24 from each well into a suitable disposal container for used needles and syringes. The spring 70 then biases the ejector 40 back to the original position for reuse.

It will be appreciated by those skilled in the art that changes may be made to the embodiments described herein without departing from the scope of the invention. It is particularly noted that the features of different embodiments and claims may be combined with each other as long as they do not contradict each other. All such changes and combinations are considered to be within the scope of the invention, which is defined by the appended claims and their equivalents.

The foregoing embodiments and advantages are merely exemplary and are not to be construed as limiting the scope of the present invention. The description of an exemplary embodiment of the present invention is intended to be illustrative, and not to limit the scope of the present invention. Various modifications, alternatives, and variations will be apparent to those of ordinary skill in the art, and are intended to fall within the scope of the invention.

The invention claimed is:

1. A device for supporting at least one pen needle assembly for a pen needle delivery device, where the pen needle assembly includes an outer cover, a needle hub having a cannula and an inner shield, said device comprising:
a housing having a top wall and a side wall, said top wall having an outer top face with at least one first well for receiving the pen needle assembly, and at least one second well having a diameter less than said first well and a dimension for receiving and retaining the inner shield; and
an ejector for ejecting the outer cover and a used needle hub from the first well and for ejecting the inner shield from the second well.

2. The device of claim 1, wherein said first well has a dimension to engage the outer cover of the pen needle assembly to enable separation of the needle hub from the outer cover.

3. The device of claim 1, wherein said first well has a shape and dimension complementing a shape and dimension of the outer cover to grip the outer cover with sufficient force to enable separation of the needle hub from the outer cover and to inhibit rotation of the outer cover within the first well.

4. The device claim 3, wherein said first well includes a rib oriented for mating with a complementing recess on the outer cover to inhibit the rotation of the outer cover relative to the housing.

5. The device of claim 1, wherein said second well has a dimension to engage the inner shield to enable separation of the needle hub from the inner shield.

6. The device of claim 5, wherein said second well has an inner surface to grip the inner shield by a friction fit.

7. The device of claim 1, wherein said ejector is movable from a first position to a second position, said ejector including a first plunger cooperating with said first well and a second plunger cooperating with said second well whereby movement of said ejector from said first position to said second position ejects the outer cover and a used needle hub from said first well and ejects said inner shield from said second well.

8. A storage device for supporting a plurality of pen needle assemblies for a pen needle delivery device, where each pen needle assembly includes an outer cover, a needle hub having a cannula and an inner shield, said device comprising:
a housing having a top wall and a side wall, said top wall having an outer top face with a plurality of first wells for receiving the pen needle assembly, and a plurality of second wells having a diameter less than said first wells and a dimension for receiving and retaining the inner shield; and
a movable ejector for ejecting the outer cover and a used needle hub from the first well and for ejecting the inner shield from the second well.

9. The device of claim 8, wherein said first wells have a dimension to engage and retain the outer cover of the pen needle assembly in the first well to enable separation of the needle hub from the outer cover.

10. The device of claim 8, wherein said first wells have a shape and dimension complementing a shape and dimension of the outer cover to grip the outer cover with sufficient force to enable separation of the needle hub from the outer cover and to inhibit rotation of the outer cover within the first well.

11. The device claim 10, wherein said first wells includes a rib oriented for mating with a complementing recess on the outer cover to inhibit the rotation of the outer cover relative to the well and housing.

12. The device of claim 8, wherein said second wells have a dimension to engage the inner shield to enable separation of the needle hub from the inner shield.

13. The device of claim 12, wherein said second well has an inner surface to grip the inner shield by a friction fit.

14. The device of claim 1, wherein said ejector is movable from a first position to a second position, said ejector including a first plunger for cooperating with and for sliding in a respective first well and a second plunger for cooperating with and sliding in a respective second well whereby movement of said ejector from said first position to said second position ejects the outer cover and a used needle hub from each said first well and ejects said inner shield from each said second well.

15. A method of coupling and uncoupling a needle hub with respect to a pen needle delivery device for delivering a substance to a patient, said method comprising the steps of:
providing a support device having a housing with plurality of first wells with a dimension for receiving an outer cover and needle hub of a pen needle assembly, a plurality of second wells having a dimension for receiving an inner shield of the pen needle assembly;
inserting the pen needle assembly into one of said first wells and coupling to a coupling end of the needle hub;
removing said pen needle delivery device and needle hub from the first well;
inserting an inner shield coupled to the needle hub into a second well of said device, where said second well is spaced from said first well, where said inner shield is gripped by said second well, and separating said needle hub from said inner shield for use in delivering the substance to the patient; and
positioning the resulting used needle hub in said outer cover retained in the first well and uncoupling said needle hub from said pen needle delivery device.

16. The method of claim 15, wherein said outer cover includes a removable seal covering said needle hub, and said method comprises removing said seal before inserting said pen needle assembly into said first well.

17. The method of claim 15, wherein said ejector is movable with respect to the housing, said ejector having a plurality of first plungers oriented for sliding in a corresponding first well and a plurality of second plungers oriented for sliding in a corresponding second well, said method comprising actuating the ejector to slide said first and second plungers to eject an outer cover and used needle hub from the first wells and to eject the inner shields from the second wells.

* * * * *